United States Patent
Margarito et al.

(10) Patent No.: US 11,813,077 B2
(45) Date of Patent: Nov. 14, 2023

(54) ARRHYTHMIC HEARTBEAT RESILIENT SLEEP APNEA DETECTION

(71) Applicant: KONINKLIJKE PHILIPS N.V., Eindhoven (NL)

(72) Inventors: Jenny Margarito, Eindhoven (NL); Koen Theo Johan De Groot, Sevebum (NL); Pedro Fonseca, Borgerhout (BE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 224 days.

(21) Appl. No.: 17/126,989

(22) Filed: Dec. 18, 2020

(65) Prior Publication Data
US 2021/0186416 A1    Jun. 24, 2021

(30) Foreign Application Priority Data
Dec. 23, 2019 (EP) .................................... 19219335

(51) Int. Cl.
*A61B 5/00* (2006.01)
*G16H 40/67* (2018.01)
(Continued)

(52) U.S. Cl.
CPC .......... *A61B 5/4818* (2013.01); *A61B 5/0205* (2013.01); *A61B 5/721* (2013.01); *A61B 5/725* (2013.01); *A61B 5/7264* (2013.01); *A61B 5/7278* (2013.01); *A61B 5/7282* (2013.01); *G16H 40/67* (2018.01); *G16H 50/30* (2018.01); *A61B 5/0077* (2013.01);
(Continued)

(58) Field of Classification Search
CPC ..... A61B 5/4818; A61B 5/0205; A61B 5/721; A61B 5/725; A61B 5/7264; A61B 5/7282; A61B 5/349; A61B 5/372; A61B 5/0077; A61B 5/02405; A61B 5/02416; A61B 5/11; A61B 5/7267; A61B 2562/0219; G16H 40/67; G16H 50/30
USPC ......................................................... 600/301
See application file for complete search history.

(56) References Cited

U.S. PATENT DOCUMENTS

| | | | |
|---|---|---|---|
| 10,398,381 B1 * | 9/2019 | Heneghan | ............ A61B 5/0022 |
| 2014/0275928 A1 * | 9/2014 | Acquista | ............ A61N 1/36585 600/382 |

(Continued)

FOREIGN PATENT DOCUMENTS

| | | | | |
|---|---|---|---|---|
| WO | 2016142793 A1 | 9/2016 | | |
| WO | WO-2016142793 A1 * | 9/2016 | ......... | A61B 5/02405 |

OTHER PUBLICATIONS

Alvarez-Estevez D, Moret-Bonillo V. Spectral Heart Rate Variability analysis using the heart timing signal for the screening of the Sleep Apnea-Hypopnea Syndrome. Comput Biol Med. Apr. 1, 2016;71:14-23. doi: 10.1016/j.compbiomed.2016.01.023. Epub Feb. 2, 2016. PMID: 26866445. (Year: 2016).*

(Continued)

*Primary Examiner* — Carl H Layno
*Assistant Examiner* — Michael J Lau

(57) ABSTRACT

A method for generating sleep apnea information for a portion of body sensor data. The method of generating sleep apnea information is made dependent upon a determined presence or absence of arrhythmia within the portion of body sensor data. A first sleep apnea detection methodology is used in response to an absence of arrhythmia being detected within the portion of body sensor data.

13 Claims, 4 Drawing Sheets

(51) Int. Cl.
G16H 50/30 (2018.01)
A61B 5/0205 (2006.01)
A61B 5/349 (2021.01)
A61B 5/372 (2021.01)
A61B 5/024 (2006.01)
A61B 5/11 (2006.01)

(52) U.S. Cl.
CPC ....... A61B 5/02405 (2013.01); A61B 5/02416 (2013.01); A61B 5/11 (2013.01); A61B 5/349 (2021.01); A61B 5/372 (2021.01); A61B 5/7267 (2013.01); A61B 2562/0219 (2013.01)

(56) References Cited

U.S. PATENT DOCUMENTS

| | | | |
|---|---|---|---|
| 2015/0057512 A1* | 2/2015 | Kapoor | A61B 5/02405 600/513 |
| 2015/0106020 A1* | 4/2015 | Chung | G16H 40/67 702/19 |
| 2019/0282180 A1* | 9/2019 | Babaeizadeh | A61B 5/14542 |
| 2020/0357518 A1* | 11/2020 | Musgrove | A61B 5/361 |

OTHER PUBLICATIONS

Alvarez-Estevez Diego et al: "Spectral Heart Rate Variablility Analysis Using the Heart Timing Signal for the Screening of the Sleep Apnea-Hypopnea Syndrome", Computer in Bioloy and Medicine, New York, NY, US, vol. 71, Feb. 2, 2016, pp. 14-23.
[1] Lee, Won et al. "Epidemiology of Obstructive Sleep Apnea: A Population-Based Perspective." Expert review of respiratory medicine 2.3 (2008): 349-364.
[2] Khandoker et al, "Support Vector Machines for Automated Recognition of Obstructive Sleep Apnea Syndrome from ECG Recordings", IEEE Trans Inf Technol Biomed (2009): 37-48.
[3] Hassan et al, "Computer-aided obstructive sleep apnea screening from single lead electrocardiogram using statistical and spectral features and bootstrap aggregating", Biocybernetics and Biomedical Engineering (2016), vol. 36, Issue 1: 256-266.
[4] T Penzel et al, "The Apnea-ECG Database", Computers in Cardiology (2000): 255-258.
[5] CL Chai-Coetzer et al, "The Debate Should Now Be Over. Simplified Cardiorespiratory Sleep Tests are a Reliable, Cost-saving Option for Diagnosing Obstructive Sleep Apnea.", Am J Respir Crit Care Med (2017).
[6] P. Stein et al, "Heart rate variability, sleep and sleep disorders", Sleep Medicine Reviews (2012): 47-66, 2012.
Berry et al, "Rules for Scoring Respiratory Events in Sleep: Update of the 2007 AASM Manual for the Scoring of Sleep and Associated Events", 2012.
[8] Berry, Richard B et al. "Rules for Scoring Respiratory Events in Sleep: Update of the 2007 AASM Manual for the Scoring of Sleep and Associated Events: Deliberations of the Sleep Apnea Definitions Task Force of the American Academy of Sleep Medicine." Journal of Clinical Sleep Medicine☐: JCSM☐: Official Publication of the American Academy of Sleep Medicine 8.5 (2012): 597-619.
[9] Heart Rhythm Society, Atrial Fibrillation and Sleep Apnea: What You Need to Know, 2015.
Klosh, G., et al. "The SIESTA project polygraphic and clinical database." IEEE Engineering in Medicine and Biology Magazine 20.3 (2001): 51-57.
O. Ludka, T. Konecny, and V. Somers, "Sleep apnea, cardiac arrhythmias, and sudden death.," Tex. Heart Inst. J., vol. 38, No. 4, pp. 340-343, 2011.
P. De Chazal, C. Heneghan, E. Sheridan, R. Reilly, P. Nolan, and M. O'Malley, "Automatic classification of sleep apnea epochs using the electrocardiogram," Comput. Cardiol. 2000. vol. 27 (Cat. 00CH37163), pp. 745-748, 2000.
Valenti, Giulio, and Klaas R. Westerterp. "Optical heart rate monitoring module validation study." 2013 IEEE International Conference on Consumer Electronics (ICCE). IEEE, 2013.
T. Penzel, J. McNames, a Murray, P. de Chazal, G. Moody, and B. Raymond, "Systematic comparison of different algorithms for apnoea detection based on electrocardiogram recordings.," Med. Biol. Eng. Comput., vol. 40, No. 4, pp. 402-407, 2002.

* cited by examiner

ARRHYTHMIC HEARTBEAT RESILIENT SLEEP APNEA DETECTION

FIELD OF THE INVENTION

The present invention relates to the field of sleep apnea detection.

BACKGROUND OF THE INVENTION

Sleep apnea is a general term used to designate two types of sleep breathing disorders, namely obstructive sleep apnea (OSA) and central sleep apnea (CSA). A combination of these two disorders is usually referred to as "mixed apnea". Both of these disorders are associated with reductions (hypopneas) or complete cessations (apneas) in airflow. This leads to a decrease in blood oxygen saturation, and an eventual cortical arousal and associated burst in sympathetic activity, together with increased heart rate and blood pressure.

Sleep apnea is often underdiagnosed, due to the limited availability of sleep laboratories and the high costs associated with sleep studies. It is widely recognized that underdiagnosed sleep apnea is an important risk factor in the development of cardiovascular disease, impairment in thinking and diabetes. There is therefore a desire to provide effective and low-cost methods of identifying the occurrence of sleep apnea.

State-of-the art sleep apnea detection methods include processing heart rate information, such as heart rate variability, in order to detect the occurrence of sleep apnea. In particular, a so-called Apnea-Hypopnea Index (AHI) can be generated that indicates the occurrence and severity of apnea events during sleep.

WO2016/142793A1 discloses a portable electronic device for processing a signal acquired from a living body. It allows automatic detection of biological parameters indicative of sleep behaviour disorders (for example, of the RBD type) and, preferably, sleep apnea, for largescale screening applications.

US2019/282180A1 discloses a method and apparatus for determining respiratory information for a subject.

There is an ongoing desire to improve the accuracy and robustness of sleep apnea detection.

SUMMARY OF THE INVENTION

The invention is defined by the claims.

According to examples in accordance with an aspect of the invention, there is provided a computer-implemented method for generating sleep apnea information about a subject.

The computer-implemented method comprises: obtaining, from at least one body sensor monitoring the subject, a portion of body sensor data responsive to the occurrence of sleep apnea and the occurrence of an arrhythmic heartbeat; processing the portion of body sensor data, using an arrhythmia detection methodology, to determine whether the portion of body sensor data indicates the presence or absence of an arrhythmic heartbeat; in response to determining that the portion of body sensor data indicates the absence of an arrhythmic heartbeat, processing at least the portion of body sensor data using a first sleep apnea detection methodology to thereby generate sleep apnea information; and in response to determining that the portion of body sensor data indicates the presence of an arrhythmic heartbeat, processing the portion of body sensor data using a second, different sleep apnea detection methodology to thereby generate sleep apnea information.

The present invention recognizes that the accuracy of sleep apnea detection methodologies is negatively affected during arrhythmic heartbeats of the subject, e.g. when a subject is undergoing atrial fibrillation. In particular, it has been identified that an arrhythmic heartbeat may cause a standard sleep apnea detection methodology to incorrectly classify a portion of body sensor data (for a patient suffering from sleep apnea) as indicating the absence of sleep apnea (i.e. generate a false negative).

The present invention proposes to filter out portions or segments of body sensor data during which an arrhythmic heartbeat is detected, to thereby avoid such portions being processed by the first sleep apnea detection methodology. This thereby reduces the false negative rate of the sleep apnea detection methodology.

This concept also enables sleep apnea detection methodologies trained upon a global population (e.g. not necessarily suffering from arrhythmic heart conditions) to be used, in order to increase the accuracy of detecting the occurrence of sleep apnea. In other words, the first sleep apnea detection methodology may be trained using sensor data that is free from episodes of arrhythmic heartbeats, e.g. from a global population.

The proposed approach enables the generation of sleep apnea information that has a reduced false negative rate.

The sleep apnea information may indicate whether the portion of body sensor data indicates the presence of sleep apnea, indicates the absence of sleep apnea or whether the presence/absence of sleep apnea cannot be reliably determined (i.e. the sleep apnea status is unknown). In other words, the sleep apnea information may provide three possible pieces of information: "Sleep Apnea Detected", "No Sleep Apnea Detected" or "Sleep Apnea State Unknown".

The present invention further proposes to, when an arrhythmic heartbeat is detected, process the portion of body sensor data using a different sleep apnea detection methodology, e.g. one that has been trained using sensor data in which an arrhythmic heartbeat is present.

Using two separate sleep apnea detection methodologies enables the accuracy of generating sleep apnea information to be increased significantly.

The at least one body sensor may comprise an electrocardiography, ECG, sensor, a photoplethysmography, PPG, sensor, an accelerometer and/or a camera. Such body sensors are particularly advantageous for long-term monitoring of the subject because of their minimal intrusiveness and responsiveness to both sleep apnea and arrhythmia. In some embodiments, the at least one body sensor comprises an electroencephalography (EEG) sensor.

The computer-implemented method may further comprise a step of obtaining, from a movement sensor monitoring a movement of the subject, a portion of movement data temporally corresponding to the portion of body sensor data, wherein the step of processing the portion of body sensor data using a first sleep apnea detection methodology comprises: processing the portion of movement data using a movement artefact detection methodology, to determine whether the portion of movement data indicates the presence or absence of movement artefacts; and in response to determining that the portion of movement data indicates the absence of movement artefacts, processing the corresponding portion of body sensor data using a sleep apnea classification methodology to generate sleep apnea information indicating whether the portion of body sensor data indicates the occurrence or non-occurrence of sleep apnea.

It has also been herein recognized that movement of a subject could also affect the accuracy of a sleep apnea classification methodology. This embodiment therefore monitors movement of the subject, and determines whether a movement of the subject may have affected the body sensor data (and therefore the accuracy of a sleep apnea classification methodology).

In some embodiments, in response to determining that the portion of movement data indicates the presence of movement artefacts, the method comprises generating sleep apnea information that indicates that the presence or absence of sleep apnea cannot be reliably determined.

The computer-implemented method may further comprise a step of obtaining, from a movement sensor monitoring a movement of the subject, a portion of movement data temporally corresponding to the portion of body sensor data, wherein the first sleep apnea detection methodology comprises using a sleep apnea classification methodology to process the portion body sensor data and the portion of movement data to generate sleep apnea information indicating whether the portion of body sensor data indicates the occurrence or non-occurrence of sleep apnea.

Movement of a subject may indicate the occurrence of non-occurrence of sleep apnea. The combination of movement and body sensor data it particularly advantageous in increasing an accuracy of detecting the occurrence or non-occurrence of sleep apnea.

Embodiments may further comprise a step of obtaining subject characteristics of the subject, wherein the step of processing the portion body sensor data using a first sleep apnea detection methodology comprises processing at least the portion of body sensor data and the subject characteristics using the first sleep apnea detection methodology.

It has also been identified that using characteristics of the subject can also improve the accuracy of a sleep apnea detection methodology. In particular, it has been identified that characteristics of a subject can influence the susceptibility or propensity of that subject to suffer from sleep apnea.

In at least one embodiment, the subject characteristics comprise physical or demographic characteristics of the subject and/or a patient history of the subject.

In particular, subject characteristics that have been identified as being related to sleep apnea include: body mass index; neck circumference; age; weight; height and gender. The patient history may indicate historic signs/symptoms/ diagnoses of the subject, which have been identified as being related to sleep apnea, for example: loud snoring; daily sleepiness and/or sense of fatigue.

In some embodiments, the step of obtaining, from at least one body sensor monitoring the subject, a portion of body sensor data comprises: obtaining a portion of raw sensor data from the at least one body sensor; and processing the portion of raw sensor data using a low-pass filter to obtain the portion of body sensor data.

Pre-processing the raw body sensor data using a low-pass filter can help remove baseline changes and artefacts from the raw body sensor data, thereby improving detection of the presence or absence of sleep apnea.

Preferably, the arrhythmia detection methodology is adapted to detect the presence or absence of atrial fibrillation. Atrial fibrillation has been identified as having a particularly large influence on the accuracy of a sleep apnea detection methodology, in particular increasing the false negative rate of the sleep apnea detection methodology.

The body sensor data preferably comprises heart rate variability data.

There is also proposed a computer program product comprising computer program code which, when executed on a computing device having a processing system, causes the processing system to perform all of the steps of any herein described method.

There is also proposed a sleep apnea detection module for generating sleep apnea information about a subject. The sleep apnea detection module is adapted to: obtain, from at least one body sensor monitoring the subject, a portion of body sensor data responsive to the occurrence of sleep apnea and the occurrence of an arrhythmic heartbeat; process the portion of body sensor data, using an arrhythmia detection methodology, to determine whether the portion of body sensor data indicates the presence or absence of an arrhythmic heartbeat; and in response to determining that the portion of body sensor data indicates the absence of an arrhythmic heartbeat, process the portion of body sensor data using a first sleep apnea detection methodology to thereby generate sleep apnea information.

There is also proposed a sleep apnea detection system comprising: any herein described sleep apnea detection module; and one or more body sensors adapted to monitor the subject and obtain body sensor data responsive to the occurrence of sleep apnea and the occurrence of an arrhythmic heartbeat.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

Figure 1:
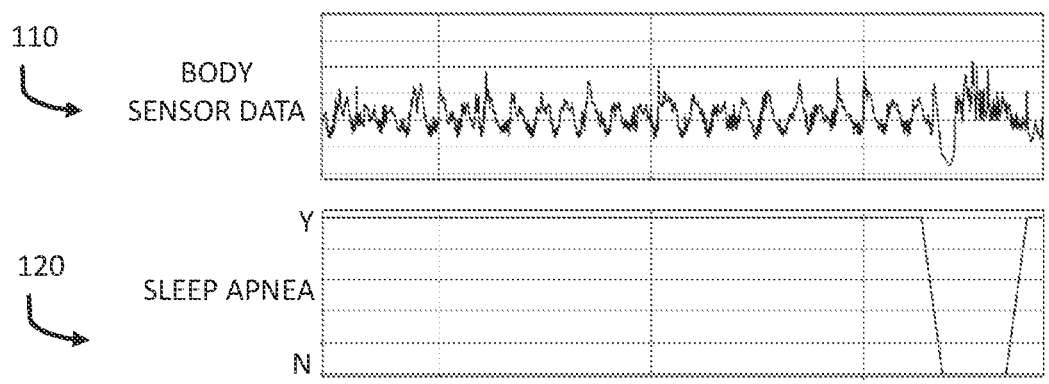
FIG. 1 illustrates a result of applying an existing sleep apnea detection method to example body sensor data for a subject without arrhythmia.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

Embodiments of the invention provide a method for generating sleep apnea information for a portion of body sensor data. The method of generating sleep apnea information is made dependent upon a determined presence or absence of arrhythmia within the portion of body sensor data. A first sleep apnea detection methodology is used in response to an absence of arrhythmia being detected within the portion of body sensor data.

The present invention relates to a concept of generating sleep apnea information related to a portion of body sensor data. The intention of the sleep apnea information is to enable identification of the presence or absence of sleep apnea in a subject during the period of time covered by the portion of body sensor data.

The present invention recognizes that there is a strong preference for avoiding false positive and/or false negative determination of the presence/absence of sleep apnea. This is particularly important in preventing misdiagnosis or mistreatment by a clinician relying upon any produced sleep apnea information.

The present invention proposes methods of reducing the occurrence of at least false negative determinations of sleep apnea, by recognizing that arrhythmia of a subject increases the false negative rate of current state-of-the-art sleep apnea detection systems.

The present invention proposes to use a different approach for assessing the presence/absence of sleep apnea if a conventional sleep apnea detection system would be made unreliable and relies upon the underlying recognition that the presence of arrhythmia affects the accuracy of a sleep apnea detection methodology, and therefore propose to use the detection of arrhythmia to control the method of generating sleep apnea information.

Figure 2:
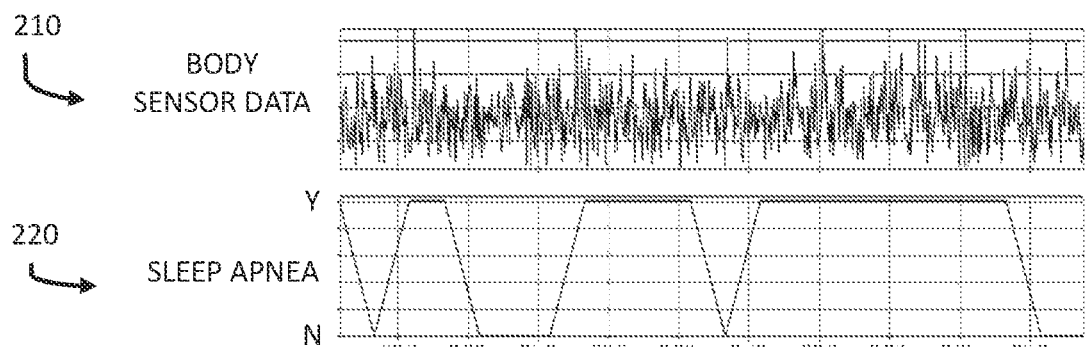
FIG. 2 illustrates a result of applying an existing sleep apnea detection method to example body sensor data for a subject having arrhythmia.

FIGS. 1 and 2 are together used to illustrate the underlying recognition of the present invention.

FIG. 1 illustrates first body sensor data 110, here heart rate variability data, obtained by monitoring a first subject/individual with a body sensor. The first subject does not have an arrhythmic heartbeat, but does suffer from sleep apnea.

FIG. 1 also illustrates a result 120 of processing the first body sensor data 110 using a conventional sleep apnea classification algorithm, which is designed to indicate whether the sleep apnea is detected in the heart rate variability data 110 (indicated by symbol "Y") or not detected in the heart rate variability data 110 (indicated by symbol "N").

FIG. 2 also illustrates second body sensor data 210, which is again heart rate variability data, obtained by monitoring a second subject/individual with a body sensor. The second subject has an arrhythmic heartbeat, e.g. caused by atrial fibrillation (AF), and suffers from sleep apnea.

FIG. 2 also illustrates a result 220 of processing the second body sensor data 110 using the same conventional sleep apnea classification algorithm, which is designed to indicate whether the sleep apnea is detected in the heart rate variability data 110 (indicated by symbol "Y") or not detected in the heart rate variability data 110 (indicated by symbol "N").

As can be seen from FIG. 2, the false negative rate for detecting sleep apnea for the second subject is greater than for the first subject. Thus, the accuracy of the sleep apnea detection system has been affected by the presence of an arrhythmic heartbeat.

The present invention recognizes that the presence of simultaneous sleep apnea and arrhythmic heartbeats causes the body sensor data to be affected so that the accurate detection of sleep apnea is no longer possible. In particular, a false negative rate for detecting sleep apnea is affected, which would lead to false estimation of the AHI index (if calculated).

This effect is particularly pronounced in heart rate variability (HRV) data. In HRV data, periodic oscillations are characteristic of sleep apnea. Thus, sleep apnea can be identified by searching for periodic oscillations in HRV data. However, the presence of arrhythmic heartbeat disrupts the regularity of the HRV data, thus falsely causing a sleep apnea detection method to detect an absence of sleep apnea.

The present invention proposes methods for handling the conflict between sleep apnea and the presence of arrhythmic heart rate, e.g. caused by atrial fibrillation.

Figure 3:
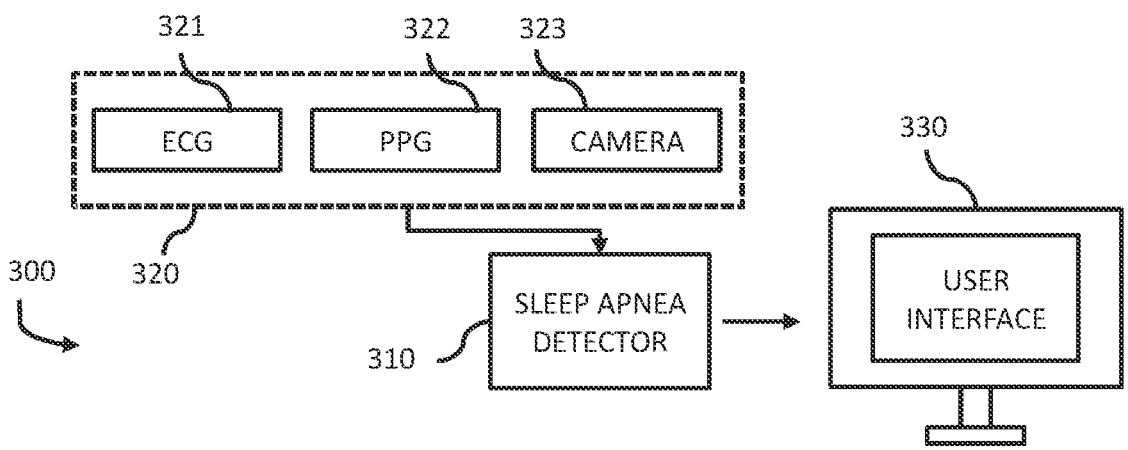
FIG. 3 illustrates a sleep apnea detection system according to an embodiment.

FIG. 3 illustrates a sleep apnea detection system 300 according to an embodiment. The sleep apnea detection system comprises a sleep apnea detection module 310, a set 320 of one or more sensors 321, 322, 323 and a (optional) user interface 330. The sleep apnea detection module 310 is itself considered an embodiment of the invention.

The sleep apnea detection module 310 is adapted to obtain one or more portions of body sensor data from the set 320 of one or more sensors. The sleep apnea detection module 310 processes a portion of the body sensor data to detect the presence or absence of arrhythmia. In response to detecting the absence of arrhythmia, the sleep apnea detection module processes the portion of body sensor data using a first sleep apnea detection methodology to generate sleep apnea information.

More complete examples of the operation of the sleep apnea detection module will be provided later, when discussing methods according to embodiments of the invention.

The set 320 of one or more sensors 321, 322, 323 is adapted to generate body sensor data responsive to both arrhythmia and sleep apnea. This data is obtained during the course of a subject's sleep, and may include, for example, heart rate or heart rate variability data, accelerometer data, ECG/EEG data and so on. Suitable examples of sensors are illustrated, and may include one or more of: an electrocardiography, ECG, sensor 321, a photoplethysmography, PPG, sensor 322, an accelerometer, an EEG system and/or a camera 323. A camera may, for example, monitor color changes of the subject in order to derive heartrate information. Other suitable examples would be well known to the skilled person.

The set 320 of one or more sensors may be further adapted to generate additional data, e.g. that is not responsive to both arrhythmia and sleep apnea. This may include, for example, respiratory data, which could be obtained using a camera, accelerometer or other sensor (which may form part of the set 320 of one or more sensors). This information may be used to enhance the accuracy of identifying sleep apnea, as will be later explained.

The user interface 330 is used to display information about whether or not sleep apnea is detected by the sleep apnea detection module 310. This may comprise, for example, displaying a report on the development of sleep apnea information generated during the course of a subject's sleep.

Figure 4:
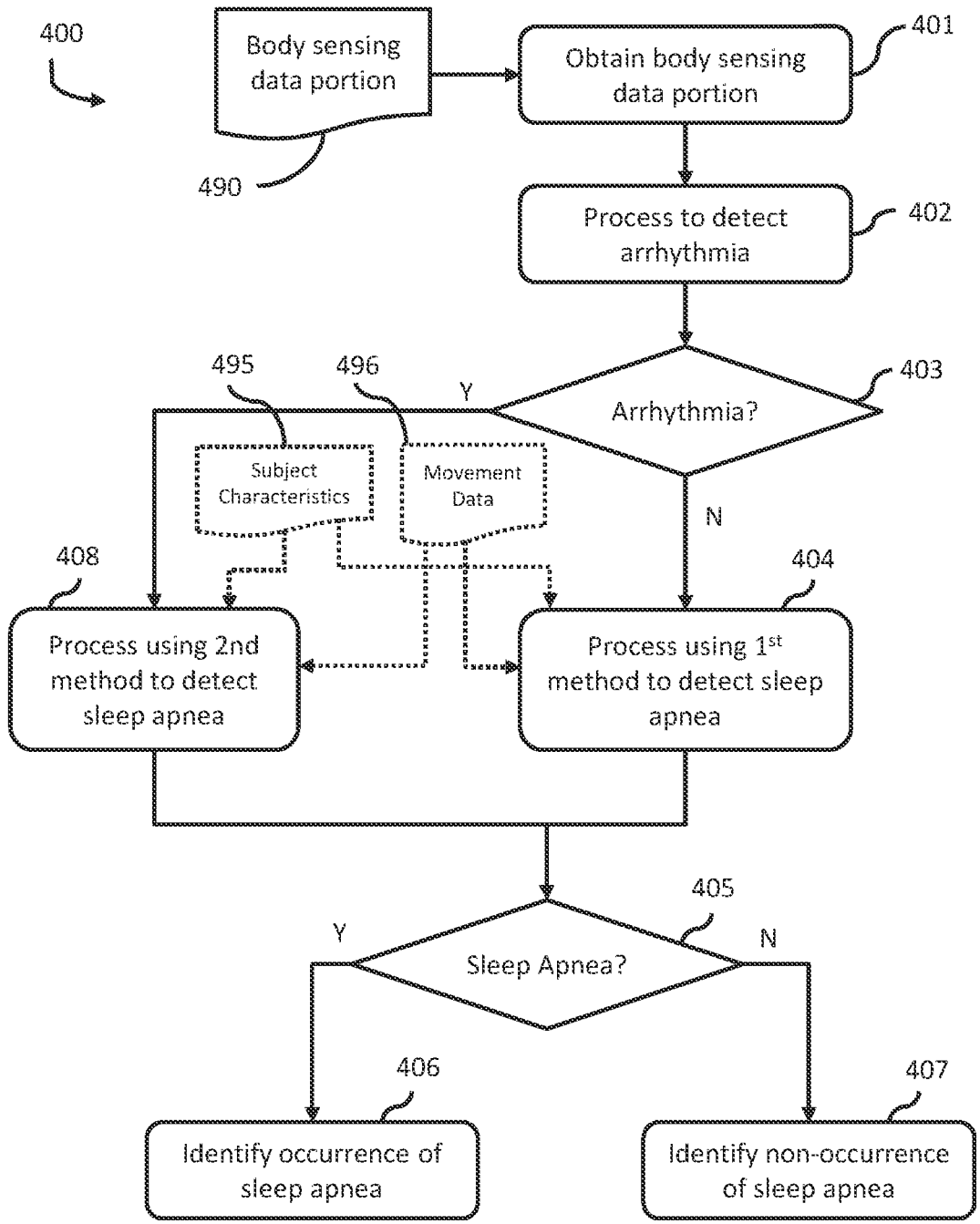
FIG. 4 illustrates a method for generating sleep apnea information according to an embodiment.

FIG. 4 illustrates a method 400 according to an embodiment of the invention.

The method 400 comprises a step 401 of obtaining a portion of body sensor data 490. The body sensor data may be obtained directly from one or more sensors monitoring a subject, or a database storing information obtained from the one or more sensors. As previously explained, the portion of body sensor data is responsive to the presence (or absence) of both arrhythmia and sleep apnea.

It will be clear that the portion of body sensor data corresponds to body sensor data obtained over a period of time, i.e. may vary with respect to time.

Of course, the portion of body sensor data may comprise information extracted from different sources (e.g. heart rate information and respiratory information). Not all of the portion of body sensor data needs to be responsive to both arrhythmia and sleep apnea, provided at least some of the body sensor data is responsive to arrhythmia and sleep apnea (e.g. the heart rate information alone).

The portion of body sensor data may, for example, be derived from a window or epoch of raw body sensor data (e.g. a most recently obtained portion of raw body sensor data).

In some embodiments, step 401 comprises obtaining a portion of raw sensor data from the at least one body sensor and processing the portion of raw sensor data using a (digital) low-pass filter to obtain a portion of body sensor data. In other words, step 401 may comprise pre-processing the portion of body sensor data using a (digital) low pass filter. This reduces the effect of baseline changes and artefacts in the portion of body sensor data.

The method 400 further comprises a step 402 of processing the portion of body sensor data, using an arrhythmia detection methodology. The method then determines in a decision step 403 whether the portion of body sensor data indicates the presence or absence of an arrhythmic heartbeat (i.e. as a result of the processing).

Processing the portion of body sensor data may be performed using a machine-learning method, e.g. a trained classifier. The classifier may be adapted to predict whether or not the portion of body sensor data indicates the presence of an arrhythmic heartbeat (i.e. arrhythmia).

In response to the portion of body sensor data indicating the absence of an arrhythmic heartbeat, the method moves to a step 404 of processing the portion of body sensor data using a first sleep apnea detection methodology to thereby generate sleep apnea information.

In particular, step 404 comprises processing the portion of body sensor data using a first sleep apnea detection methodology. The method then performs a decision step 405 to determine whether the portion of body sensor data indicates the presence or absence of sleep apnea. In response to detecting the presence of sleep apnea, the method performs step 406 of generating sleep apnea information that indicates that the portion indicates the occurrence of sleep apnea, e.g. by providing a "Present" output as the sleep apnea information. In response to detecting the absence of sleep apnea, the method performs step 407 of generating sleep apnea information that indicates that the portion indicates the absence of sleep apnea, e.g. by providing an "Absent" output as the sleep apnea information.

Other forms of sleep apnea information indicating the presence or absence of sleep apnea could be generated, e.g. generating a probability of the presence of sleep apnea or the like.

When step 405 is performed after step 404, step 405 uses information obtained from the first sleep apnea detection methodology to make the determination.

A number of different actions may be performed in response to steps 402-403 determining that the portion of body sensor data indicates the presence of an arrhythmic heartbeat, suitable examples of which will be described later. However, it should be clear that the process performed in response to the presence of an arrhythmic heartbeat is different to the process performed in response to the absence of an arrhythmic heartbeat, e.g. omitting certain steps, including additional steps or performing another process altogether.

In one embodiment, in response to determining that the portion of body sensor data indicates the presence of an arrhythmic heartbeat, the method 400 performs a step 408 of processing the portion of body sensor data using a second, different sleep apnea detection methodology to thereby generate sleep apnea information. The second sleep apnea detection methodology is different to the first sleep apnea detection methodology, e.g. has been trained using different data and/or makes use of different features or elements of the portion of body sensor data and so on.

In this embodiment, the portion of body sensor data including arrhythmic heartbeat may be used to determine a type of arrythmia. A type of arrythmia classifier may be trained by using machine learning techniques such as deep learning and/or features based approach. The portion of body sensor data and/or statistical and morphological features extracted from the body sensor data may be used as input to the type of arrythmia classifier. Type of arrythmia may include any of atrial flutter, atrial fibrillation, ventricular fibrillation, premature atrial contractions, supraventricular tachycardia, ventricular tachycardia, sick sinus syndrome, supraventricular arrhythmias, premature ventricular complex. The second sleep apnea detection methodology may include different approaches for each type of arrythmia. The portion of body sensor data including arrhythmic heartbeat may be selected and labeled based on the information whether the sleep apnea event is detected or not in the remainder of the body sensor data. The portion of body sensor data or extracted features in combination with their label (APNEA-NO APNEA) may be provided as input the machine learning algorithm which is based on a supervised learning approach to learn whether segments of the body sensor data hide sleep apnea events or not. After determining which type of arrhythmia is present in the portion of the body sensor data, corresponding algorithm is deployed by the second sleep apnea detection methodology. Determining the presence or absence of a condition (such as an arrhythmic heartbeat, sleep apnea or type of arrythmia) may comprise determining a probability of the presence of the condition. Probability of the presence of a sleep apnea may be determined based on the determined probability of the presence of arrythmia and/or the type of arrythmia. Information on the determined probability of a presence of a condition may be provided to a user, e.g. contained within the sleep apnea information.

The method 400 then moves from step 408 to step 405. When step 405 is performed after step 408, step 405 uses information obtained from the second sleep apnea detection methodology to make the decision as to whether sleep apnea is detected or not.

One or more of steps 402 and 404 may be performed by deriving one or more (statistical) features from the portion of body sensor data, and processing the features using a pre-trained classification model to determine the presence or absence of arrhythmia or sleep apnea (where appropriate).

In some embodiments, the features are extracted directly from the portion of body sensor data. In other embodiments, the features are extracted from information derived from the portion of body sensor data.

Consider an example in which the portion of body sensor data is derived in step 401 from a portion of heart rate data, e.g. measured by an ECG or PPG sensor, obtained from the subject.

The derivation of features may comprise using a beat detector to detect the heartbeat in the portion of heart rate data and identify the interbeat intervals (IBIs), i.e. to generate an IBI time series. In the case of an ECG sensor, this can be performed using a QRS detector, which identifies and locates R-peaks. In the case of a PPG sensor, this detector can instead detect individual heartbeats by localizing the peak amplitude, or the foot of an increase pulse. The (statistical) features may then be extracted from the series of IBIs, to thereby obtain features from the portion of body sensor data.

A pre-trained classification model, for detecting arrhythmia and/or sleep apnea, may have been built by deploying a machine learning approach, and may be used to process (statistical) features derived from the portion of body sensor data, e.g. extracted from an IBI time series.

In one example, the arrhythmia classification model comprises a logistic regression classifier. This is particularly advantageous because of its simplicity and interpretability. However, any suitable machine-learning algorithms could be employed. Examples of suitable machine-learning algorithms include decision tree algorithms and artificial neural networks. Other machine-learning algorithms such as support vector machines, Random Forest or Naïve Bayesian model are suitable alternatives.

Further examples of suitable machine-learning algorithms will be described later.

The features extracted in any of steps 402 and 404 do not need to be identical to one another. Thus, the features used for detecting sleep apnea may be different to the features used for detecting arrhythmia. Similarly, the features used for detecting sleep apnea may differ depending upon whether or not arrhythmia is detected.

By way of example only, the portion of body data may include some information that is responsive to sleep apnea, but not arrhythmia (e.g. respiratory data or the like). The features extracted for detection of sleep apnea may correspond to features of such information.

By way of another example, training of a machine-learning algorithm may result in different features being identified for use in detection of sleep apnea and detection of arrhythmia.

Turning back to FIG. 4, in some embodiments the (first and optionally second) sleep apnea detection methodology may use additional information of the subject to detect the presence or absence of sleep apnea.

By way of example, characteristics of the subject 290 may be used to refine the sleep apnea detection methodology. The characteristics of the subject may be provided as input to a sleep apnea detection methodology, or could be used to select which of a plurality of possible sleep apnea detection methodologies are used to process the portion of body sensor data.

Suitable subject characteristics include: body mass index; neck circumference; age, gender, height and/or weight. Any suitable parameter derived using the aforementioned characteristics (e.g. a calculated body mass index from height, gender and weight) may also be used.

A patient history may also be used in a similar manner to the subject characteristics. The patient history may indicate historic signs/symptoms/diagnoses of the subject, and in particular those that have been identified as being related to sleep apnea, for example: loud snoring; daily sleepiness and/or sense of fatigue. This information can be used to improve the detection and of sleep apnea using the portion of body sensor data.

Additional information obtained from the set of one or more sensors monitoring the subject, e.g. generating respiratory information, may be used to improve the detection of the presence or absence of sleep apnea, as would be apparent to the skilled person.

As another example, movement data may be used to improve the prediction of sleep apnea. Movement of the subject can affect the accuracy of detecting the occurrence of sleep apnea, e.g. by a movement introducing artefacts into the body sensor data. Moreover, movement of the subject may be indicative of sleep apnea, e.g. due to a subject temporally waking up do to a sleep apnea event.

Movement data may be obtained from the set of one or more sensors, e.g. an accelerometer or pressure sensor connected to the subject or their surroundings.

Movement data of the subject may also be used to determine whether or not a sleep apnea detection methodology is able to reliably detect the presence/absence of sleep apnea.

Thus, in some further embodiments, the method may comprise a step of obtaining movement data temporally corresponding to the portion of body sensor data, and processing the obtained movement data to identify the presence or absence of movement artefacts (which could affect the portion of body sensor data, and thereby the accuracy/reliability of a sleep apnea detection).

In response to detecting the presence of movement artefacts the method may comprise generating apnea information that indicates that the presence or absence of sleep apnea cannot be reliably determined. Otherwise, the method may proceed as normal (i.e. as if the step of determining the presence or absence of movement artefacts had never taken place).

The process of identifying whether movement artefact(s) affect the ability to generate accurate sleep apnea information may be performed at any stage during the overall method. Preferably, it is performed before the step of determining whether the portion of body sensor data indicates the presence or absence of arrhythmia, to avoid unnecessary complex processing of the portion of body sensor data.

Alternatively, this process could be integrating into the first and/or second sleep apnea detection methodology (/ies).

Figure 5:
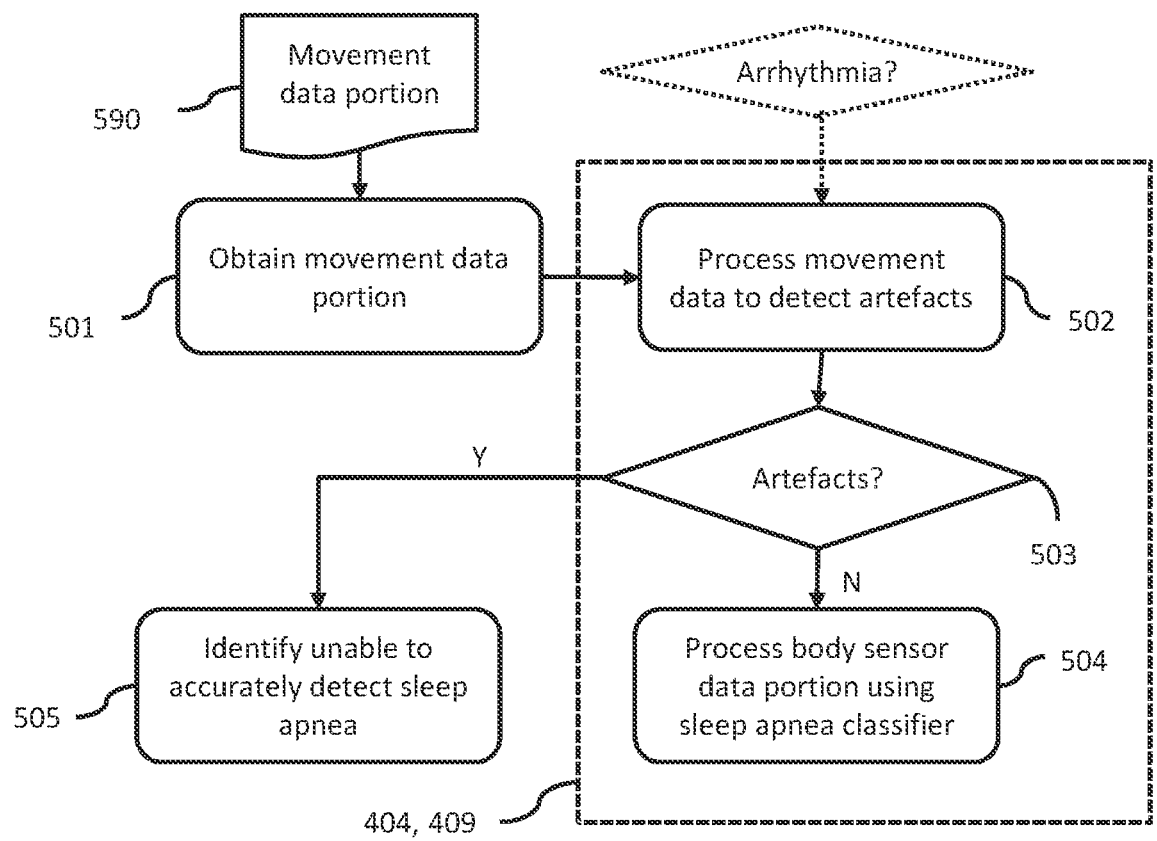
FIG. 5 illustrates a portion of a method for generating sleep apnea information according to an embodiment.

FIG. 5 illustrates one embodiment for processing a portion of body sensor data using a sleep apnea detection methodology. This process may be at least partially integrated into step 404 and/or 408 (if present) of method 400, as illustrated.

The process comprises a step 501 of obtaining a portion of movement data 590 from a movement sensor monitoring a movement of the subject. The portion of movement data temporally corresponds to the portion of body sensor data (i.e. corresponds to a same time period as the portion of body sensor data).

The process further comprises a step 502 of processing the portion of movement data using a movement artefact detection methodology, to determine whether the portion of movement data indicates the presence or absence of movement artefacts. Thus, the portion of movement data may be processed to determine whether the movement data would affect the detection of sleep apnea.

A decision step 503 decides whether or not movement artefacts were detected.

In response to no or negligible movement artefacts being detected, e.g. the number of detected movement artefacts is below a predetermined threshold, the portion of body sensor data is processed in a step 504 using a sleep apnea classification methodology to generate the sleep apnea information. The sleep apnea classification methodology may comprise any suitable sleep apnea processing methodology, such as those previously described with reference to step 404 or step 408.

In response to determining that the portion of movement data indicates the presence of movement artefacts (i.e. non-negligible amounts of movement artefacts are present), the process performs a step 505 of generating sleep apnea information that indicates that the presence or absence of sleep apnea cannot be reliably determined.

Thus, before performing a sleep apnea detection methodology, embodiments propose checking whether arrhythmia is present and/or whether movement artefacts are present. In response to either of these being present, the method moves to a step of generating sleep apnea information that indicates that the presence or absence of sleep apnea cannot be reliably determined.

In the illustrated examples, the process is performed by firstly checking for arrhythmia, and then checking for movement artefacts. However, this process may be reversed in other embodiments of the invention.

Thus, there may be provided a computer-implemented method for generating sleep apnea information about a subject, comprising: obtaining a portion of movement data of a subject; processing the portion of movement data using a movement artefact detection methodology, to determine whether the portion of movement data indicates the presence or absence of movement artefacts; in response to determining that the portion of movement data indicates the absence of movement artefacts: obtaining, from at least one body sensor monitoring the subject, a portion of body sensor data responsive to the occurrence of sleep apnea and the occurrence of an arrhythmic heartbeat, the portion of body sensor data temporally corresponding to the portion of movement data; processing the portion of body sensor data, using an arrhythmia detection methodology, to determine whether the portion of body sensor data indicates the presence or absence of an arrhythmic heartbeat; and in response to determining that the portion of body sensor data indicates the absence of an arrhythmic heartbeat, processing the portion of body sensor data using a first sleep apnea detection methodology to thereby generate sleep apnea information.

Of course, the step of obtaining the portion of body data does not need to be responsive to the determination of the portion of movement data, and could be performed in any event, e.g. alongside obtaining the corresponding portion of movement data.

In some further embodiments, the method may comprise a step of determining a quality of the portion of body sensor data. This may be performed using any suitable quality determination process, which may, for example, comprise processing the portion of body sensor data using a machine-learning method for assessing the quality of the data.

This may comprise, in a scenario in which the portion of body sensor data comprises heart rate data or accelerometer data, calculating the number of heartbeats in the portion of body sensor data. The number of heartbeats is reflective of the quality of the portion of body sensor data.

In some examples, this process may comprise determining a noise level of the portion of body portion data, e.g. a signal to noise (SNR) ratio. This enables the quality of the portion of body sensor data to be derived.

In response to the portion of body sensor data not meeting a predetermined threshold or criteria (e.g. a calculated number of heartbeats or a SNR ration being below a predetermined value), the method may comprise generating apnea information that indicates that the presence or absence of sleep apnea cannot be reliably determined. Otherwise, the method may proceed as normal (i.e. as if the step of determining the quality of the portion of body sensor data had never taken place).

This step may be performed at any time during the process, but it preferably performed before the step of determining whether the portion of body sensor data indicates the presence or absence of arrhythmia.

Thus, embodiments propose checking for the presence of arrhythmia, and optionally movement artefacts and/or suitable data quality. The process of generating sleep apnea information is responsive or different depending upon the presence and/or absence of this/these element(s).

The process of generating sleep apnea information may be performed iteratively, e.g. for different portions of body sensor data. This allows a sequence or series of portions of body sensor data to be processed, to thereby enable sleep apnea information over the course of a large period of time (e.g. a night's sleep) to be derived.

In preferable embodiments, a stream of body sensor data is obtained and a sliding window is applied to the stream of body sensor data. Each windowed portion of the body sensor data forms a portion of the body sensor data that is subsequently processed.

In one example, the length of each window is in the region of 40 to 80 seconds in length (e.g. 60 seconds), with a 20 to 40 second overlap (e.g. 30 seconds) between windows. In another example, the length of each window is in the region of 15 to 30 seconds in length (e.g. 20 seconds), with a 0.5 to 2 second (e.g. 1 second) overlap between windows. This latter embodiment enables the identification of the presence or absence of sleep apnea to occur with a finer grain of resolution.

Figure 6:
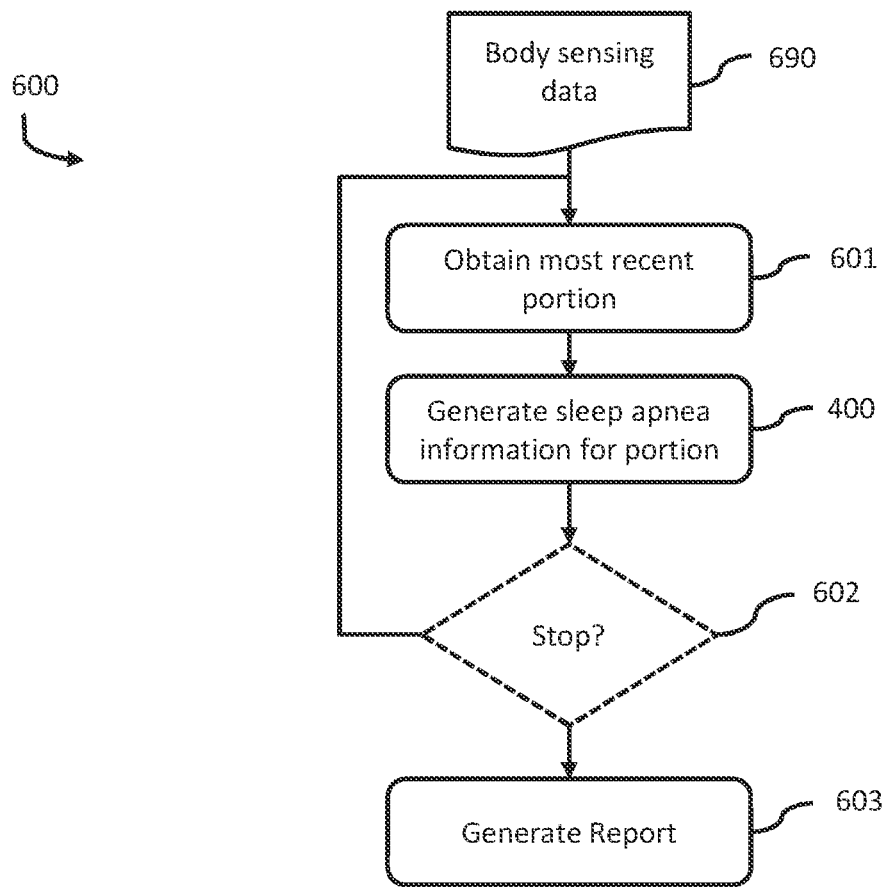
FIG. 6 illustrates a method for generating sleep apnea information according to another embodiment.

In particular, the processed portion of body sensor data may be a most recently available portion of body sensor data (e.g. representing a predetermined period of time). This process is illustrated in FIG. 6, which illustrates a method 600 of processing (a stream of) body sensing data 690.

The method 600 comprises a step 601 of obtaining a most recent portion of the body sensing data 690. The method then performs method 400 of generating sleep apnea information for the obtained portion of body sensing data.

Steps 601 and method 400 may be iteratively repeated until a stop condition is reached, as decided in a step 602. The stop condition may, for example, be a number of iterations being reached, a predetermined time period elapsing or a user input being received.

The method then moves to (optional) step 603 of generating a report for the body sensing data, that illustrates the sleep apnea information over time. Of course, a live report may be generated without needing a stop condition to be met, e.g. to illustrate the sleep apnea information up until a current period of time.

Step 603 may additionally or alternatively comprise determining an Apnea-Hypopnea Index using the sleep apnea information generated for the plurality of portions of body sensor data.

In particular, an Apnea-Hypopnea Index may be generated by excluding periods of time associated with portions of body sensor data for which a determination of the presence or absence of sleep apnea could not be determined, i.e. whether the sleep apnea status is "Unknown".

This may comprise dividing the number of times the presence of sleep apnea was detected by the length of time that the absence of sleep apnea was detected (e.g. as opposed to the presence or absence of sleep apnea being unknown or unable to be reliably calculated).

Thus, in a scenario in which 20 sleep apnea events are detected during a 480 minute period, 210 minutes of which are associated with portions of body sensor data for which it was not possible to accurately detect the occurrence or non-occurrence of sleep apnea, then the Apnea-Hypopnea Index would be calculated to be 4.4.

Figure 7:
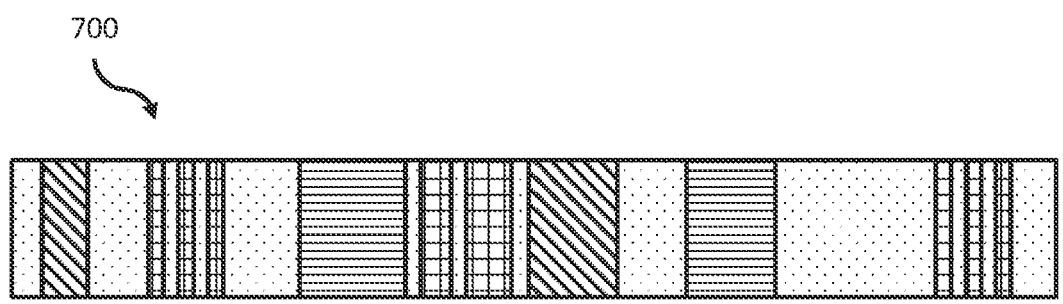
FIG. 7 illustrates a report generated by an embodiment of the invention.

FIG. 7 illustrates a suitable example of a report 700, which is represented graphically. The report provides sleep apnea information over a period of time.

Stippled (i.e. dotted) section of the report indicate times during which the absence of sleep apnea is detected. Square-hatched sections indicates times during which the presence of sleep apnea is detected. Horizontally hatched sections indicate times during which it was not possible to accurately detect the presence or absence of sleep apnea due to the occurrence of arrhythmia. Diagonally-hatched section indicate times during which it was not possible to reliably detect the presence or absence of sleep apnea due to other reasons (e.g. poor quality data).

The illustrated display properties are merely exemplary, and may be replaced by any other suitable indicator for distinguishing between sections (e.g. colors or other patterns).

Of course, in embodiments in which a second sleep apnea detection method is used when arrhythmia is detected, the "horizontally hatched" sections may be replaced by appropriately marked sections for indicating times during which the presence or absence of sleep apnea is detected. Such sections may comprise a further indicator that atrial fibrillation occurred (e.g. a certain color or saturation, compared to other sections).

In any previously described embodiment, determining the presence or absence of a condition (such as an arrhythmic heartbeat or sleep apnea) may comprise determining a probability of the presence of the condition. Steps performed in response to determining the presence of a condition may be performed in response to the determined probability exceeding a predetermined threshold (e.g. 50% or 75%). Steps performed in response to determining the absence of a condition may be performed in response to the determined probability falling below a predetermined threshold (e.g. below 50% or the like). Information on the determined probability of a presence of a condition may be provided to a user, e.g. contained within the sleep apnea information.

Previous embodiments have described how a machine-learning algorithm could be employed to process data in order to generate or predict output data. In particular, a machine-learning algorithm could be employed to process a portion of body sensor data in order to determine a presence or absence of sleep apnea or arrhythmia, to process a portion of movement data to determine a presence or absence of movement artefacts or to process a portion of body sensor data to determine a quality of the portion of body sensor data.

A machine-learning algorithm is any self-training algorithm that processes input data in order to produce or predict output data.

Suitable machine-learning algorithms for being employed in the present invention will be apparent to the skilled person. Examples of suitable machine-learning algorithms include decision tree algorithms and artificial neural networks. Other machine-learning algorithms such as logistic regression, support vector machines or Naïve Bayesian model are suitable alternatives.

The structure of an artificial neural network (or, simply, neural network) is inspired by the human brain. Neural networks are comprised of layers, each layer comprising a plurality of neurons. Each neuron comprises a mathematical operation. In particular, each neuron may comprise a different weighted combination of a single type of transformation (e.g. the same type of transformation, sigmoid etc. but with different weightings). In the process of processing input data, the mathematical operation of each neuron is performed on the input data to produce a numerical output, and the outputs of each layer in the neural network are fed into the next layer sequentially. The final layer provides the output.

Methods of training a machine-learning algorithm are well known. Typically, such methods comprise obtaining a training dataset, comprising training input data entries and corresponding training output data entries. An initialized machine-learning algorithm is applied to each input data entry to generate predicted output data entries. An error between the predicted output data entries and corresponding training output data entries is used to modify the machine-learning algorithm. This process can repeated until the error converges, and the predicted output data entries are sufficiently similar (e.g. ±1%) to the training output data entries. This is commonly known as a supervised learning technique.

For example, where the machine-learning algorithm is formed from a neural network, (weightings of) the mathematical operation of each neuron may be modified until the error converges. Known methods of modifying a neural network include gradient descent, backpropagation algorithms and so on.

Using a machine-learning method may comprise deriving or extracting one or more (statistical) features from the data provided as input, and processing the derived features in order to determine the output.

Different machine-learning methods may use different features of the same input data in order to generate their output data. This may even be the case if the machine-learning methods are intended to provide the same information as the output data (e.g. a determination of the presence or absence of sleep apnea).

Embodiments of the present invention propose to use different sleep apnea detection methodologies, e.g. machine-learned algorithms trained using different datasets, depending upon the determined presence or absence of arrhythmia. This may comprise using different machine-learning methods to process a portion of body sensor data to determine the presence or absence of sleep apnea.

The skilled person would be readily capable of developing a processing system for carrying out any herein described method. Thus, each step of the flow chart may represent a different action performed by a processing system, and may be performed by a respective module of the processing system.

Embodiments may therefore make use of a processing system. The processing system can be implemented in numerous ways, with software and/or hardware, to perform the various functions required. A processor is one example of a processing system that employs one or more microprocessors that may be programmed using software (e.g., microcode) to perform the required functions. A processing system may however be implemented with or without employing a processor, and also may be implemented as a combination of dedicated hardware to perform some functions and a processor (e.g., one or more programmed microprocessors and associated circuitry) to perform other functions.

Examples of processing system components that may be employed in various embodiments of the present disclosure include, but are not limited to, conventional microprocessors, application specific integrated circuits (ASICs), and field-programmable gate arrays (FPGAs).

In various implementations, a processor or processing system may be associated with one or more storage media such as volatile and non-volatile computer memory such as RAM, PROM, EPROM, and EEPROM. The storage media may be encoded with one or more programs that, when executed on one or more processors and/or processing systems, perform the required functions. Various storage media may be fixed within a processor or processing system or may be transportable, such that the one or more programs stored thereon can be loaded into a processor or processing system.

It will be understood that disclosed methods are preferably computer-implemented methods. As such, there is also proposed the concept of computer program comprising code means for implementing any described method when said program is run on a processing system, such as a computer. Thus, different portions, lines or blocks of code of a computer program according to an embodiment may be executed by a processing system or computer to perform any herein described method. In some alternative implementations, the functions noted in the block diagram(s) or flow chart(s) may occur out of the order noted in the figures. For example, two blocks shown in succession may, in fact, be executed substantially concurrently, or the blocks may sometimes be executed in the reverse order, depending upon the functionality involved.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. If a computer program is discussed above, it may be stored/distributed on a suitable medium, such as an optical storage medium or a solid-state medium supplied together with or as part of other hardware, but may also be distributed in other forms, such as via the Internet or other wired or wireless telecommunication systems. If the term "adapted to" is used in the claims or description, it is noted the term "adapted to" is intended to be equivalent to the term "configured to". Any reference signs in the claims should not be construed as limiting the scope.

The invention claimed is:

1. A computer-implemented method for generating sleep apnea information about a subject, the computer-implemented method comprising:
    obtaining, from at least one body sensor monitoring the subject, a portion of body sensor data responsive to the occurrence of sleep apnea and the occurrence of an arrhythmic heartbeat;
    processing the portion of body sensor data, using an arrhythmia detection methodology, to determine whether the portion of body sensor data indicates the presence or absence of an arrhythmic heartbeat;
    in response to determining that the portion of body sensor data indicates the absence of an arrhythmic heartbeat, processing the portion of body sensor data using a first sleep apnea detection methodology to generate sleep apnea information; and
    in response to determining that the portion of body sensor data indicates the presence of an arrhythmic heartbeat, processing the portion of body sensor data to determine a type of arrhythmia of the arrhythmic heartbeat and, using a second, different sleep apnea detection methodology according to the determined type of arrythmia, to generate sleep apnea information.

2. The computer-implemented method of claim 1, wherein the at least one body sensor comprises an electrocardiography, ECG, sensor, an accelerometer, an electroencephalography, EEG, sensor, a photoplethysmography, PPG, sensor and/or a camera.

3. The computer-implemented method of claim 1, further comprising a step of obtaining, from a movement sensor monitoring a movement of the subject, a portion of movement data temporally corresponding to the portion of body sensor data,
    wherein the step of processing the portion of body sensor data using a first sleep apnea detection methodology comprises:
    processing the portion of movement data using a movement artefact detection methodology, to determine whether the portion of movement data indicates the presence or absence of movement artefacts; and
    in response to determining that the portion of movement data indicates the absence of movement artefacts, processing the corresponding portion of body sensor data using a sleep apnea classification methodology to generate sleep apnea information indicating whether the portion of body sensor data indicates the occurrence or non-occurrence of sleep apnea.

4. The computer-implemented method of claim 3, wherein, in response to determining that the portion of movement data indicates the presence of movement artefacts, generating sleep apnea information that indicates that the presence or absence of sleep apnea cannot be reliably determined.

5. The computer-implemented method of claim 1, comprising a step of obtaining, from a movement sensor monitoring a movement of the subject, a portion of movement data temporally corresponding to the portion of body sensor data,
    wherein the first sleep apnea detection methodology comprises using a sleep apnea classification methodology to process the portion of body sensor data and the portion of movement data to generate sleep apnea information indicating whether the portion of body sensor data indicates the occurrence or non-occurrence of sleep apnea.

6. The computer-implemented method of claim 1, comprising a step of obtaining subject characteristics of the subject,
    wherein the step of processing the portion of body sensor data using a first sleep apnea detection methodology comprises processing at least the portion of body sensor data and the subject characteristics using the first sleep apnea detection methodology.

7. The computer-implemented method of claim 6, wherein the subject characteristics comprise physical or demographic characteristics of the subject and/or a patient history of the subject.

8. The computer-implemented method of claim 1, wherein the step of obtaining, from at least one body sensor monitoring the subject, a portion of body sensor data comprises:

obtaining a portion of raw sensor data from the at least one body sensor; and processing the portion of raw sensor data using a low-pass filter to obtain the portion of body sensor data.

9. The computer-implemented method of claim 1, wherein the arrhythmia detection methodology is adapted to detect the presence or absence of atrial fibrillation.

10. The computer-implemented method of claim 1, wherein the body sensor data comprises heart rate variability data.

11. A computing device having a processing system including a non-transitory computer program product comprising computer program code that, when executed on the computing device by the processing system, performs all of the steps of the method according to claim 1.

12. A sleep apnea detection module for generating sleep apnea information about a subject, the sleep apnea detection module being adapted to:

obtain, from at least one body sensor monitoring the subject, a portion of body sensor data responsive to the occurrence of sleep apnea and the occurrence of an arrhythmic heartbeat;

process the portion of body sensor data, using an arrhythmia detection methodology, to determine whether the portion of body sensor data indicates the presence or absence of an arrhythmic heartbeat;

in response to determining that the portion of body sensor data indicates the absence of an arrhythmic heartbeat, process the portion of body sensor data using a first sleep apnea detection methodology to generate sleep apnea information; and in response to determining that the portion of body sensor data indicates the presence of an arrhythmic heartbeat, processing the portion of body sensor data to determine a type of arrythmia of the arrhythmic heartbeat and, using a second, different sleep apnea detection methodology according to the determined type of arrythmia, to generate sleep apnea information.

13. A sleep apnea detection system comprising:

the sleep apnea detection module of claim 12; and one or more body sensors adapted to monitor the subject and obtain body sensor data responsive to the occurrence of sleep apnea and the occurrence of an arrhythmic heartbeat.

* * * * *